(12) United States Patent
Snutch

(10) Patent No.: US 6,617,322 B2
(45) Date of Patent: *Sep. 9, 2003

(54) PREFERENTIALLY SUBSTITUTED CALCIUM CHANNEL BLOCKERS

(75) Inventor: Terrance P. Snutch, Vancouver (CA)

(73) Assignee: NeuroMed Technologies, Inc., Vancouver (CA)

(*) Notice: Subject to any disclaimer, the term of this patent is extended or adjusted under 35 U.S.C. 154(b) by 0 days.

This patent is subject to a terminal disclaimer.

(21) Appl. No.: 10/060,900

(22) Filed: Jan. 29, 2002

(65) Prior Publication Data

US 2003/0045530 A1 Mar. 6, 2003

Related U.S. Application Data

(63) Continuation of application No. 09/476,927, filed on Dec. 30, 1999, now Pat. No. 6,387,897, which is a continuation-in-part of application No. 09/401,699, filed on Sep. 23, 1999, now Pat. No. 6,294,533, which is a continuation-in-part of application No. 09/107,037, filed on Jun. 30, 1998, now Pat. No. 6,011,035.
(60) Provisional application No. 60/172,831, filed on Dec. 20, 1999.

(51) Int. Cl.⁷ .................... A61K 31/535; A61K 31/495; A61K 31/445
(52) U.S. Cl. .................... 514/231.2; 514/255; 514/315
(58) Field of Search ................................ 514/231.2, 255, 514/315

(56) References Cited

U.S. PATENT DOCUMENTS

| | | | |
|---|---|---|---|
| 3,288,795 A | 11/1966 | Irikura et al. | |
| 4,188,485 A | 2/1980 | Kukla | |
| 4,918,073 A | 4/1990 | Ruger et al. | |
| 5,386,025 A | 1/1995 | Jay et al. | 536/23.5 |
| 5,428,038 A | 6/1995 | Chatterjee et al. | 514/253 |
| 5,623,051 A | 4/1997 | Catterall et al. | 530/324 |
| 5,646,149 A | 7/1997 | Hellberg et al. | 514/253 |
| 5,703,071 A | 12/1997 | Itoh et al. | 514/218 |
| 6,011,035 A * | 1/2000 | Snutch | 514/231.2 |
| 6,294,533 B1 * | 9/2001 | Snutch et al. | 514/231.2 |
| 6,387,897 B1 * | 5/2002 | Snutch | 514/231.2 |

FOREIGN PATENT DOCUMENTS

| | | |
|---|---|---|
| EP | 0 187 524 | 7/1986 |
| EP | 0 213 006 A | 3/1987 |
| EP | 0 458 387 | 11/1991 |
| ES | 504 202 | 1/1983 |
| ES | 514 167 | 4/1983 |
| GB | 1 513 883 | 6/1978 |
| WO | WO 94/14786 A | 7/1994 |
| WO | WO 99/15129 | 4/1999 |
| WO | WO 99/25686 | 5/1999 |
| WO | WO 00/01375 A | 1/2000 |
| WO | WO 00/18402 A | 4/2000 |
| WO | WO 00/37059 A | 6/2000 |

OTHER PUBLICATIONS

Bourinet et al., "Splicing of $\alpha_{1A}$ Subunit Gene Generates Phenotypic Variants of P– and Q–Type Calcium Channels," Nature Neuroscience (1992) 2:407–415.
Chiarini, A. et al. (1996). *Bioorg & Med Chemistry* 4(10):1629–1635.
Cohan, S. et al. (1991). *Annals of the New York Academy of Sciences* 635:397–399.
Cribbs et al., "Cloning and Characterization of α1H from Human Heart, A Member of the T–Type $Ca^{2+}$ Channel Gene Family," Circulation Research (1998) 83:103–109.
Database WPI Week 9711 Derwent Publications Ltd., London, GB; Abstract JP 09 003067, XP002133055 (Hisamitsu Pharm Co Ltd.) Jan. 7, 1997.
De Waard et al., "Structural and Functional Diversity of Voltage–Activated Calcium Channels," Ion Channels (Narahashi, T. ed. Plenum Press, NY 1997) 4:41–87.
Dhainaut et al. (1992). *J of Medicinal Chemistry* 35:2481–2496.
Dooley, "Lomorizine Kanebo KK" Current Opinion in CPNS Investigational Drugs (1999) 1(1):116–125.
Dunlap et al., "Exocytotic $Ca^{2+}$ Channels in Mammalian Central Neurons," Trends Neurosci (1995) 18:89–98.
Estep, K. et al. (1995). *J of Medicinal Chemistry* 38(14):2582–2595.

(List continued on next page.)

Primary Examiner—Raymond Henley, III
(74) Attorney, Agent, or Firm—Morrison & Foerster LLP

(57) ABSTRACT

Compounds of the formula

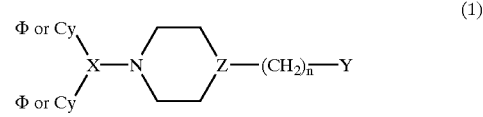

(1)

and their salts,
wherein Cy represents cyclohexyl;
Y is CH=CHΦ, CHΦ₂, Φ or Cy,
X is trivalent straight-chain alkylene (3–10C) or trivalent straight-chain 1-alkenylene (3–10C) optionally substituted by oxo at the C adjacent N when n is 0 and Y is Φ₂CH; and is otherwise trivalent straight-chain alkylene (5–10C) or trivalent straight-chain 1-alkenylene (5–10C) optionally substituted by oxo at the C adjacent N;
Z is N, NCO, CHNCOR¹ or CHNR¹, wherein R¹ is alkyl (1–6C); and
n is 0–5;
wherein each Φ and Cy independently may optionally be substituted by alkyl (1–6C) or by halo, CF₃, OCF₃, NO₂, NR₂, OR, SR, COR, COOR, CONR₂, NROCR or OOCR where R is H or alkyl (1–4C), or two substituents may form a 5–7 membered ring
with the proviso that the compounds of formula (1) contain at least one aromatic moiety,
are useful as calcium channel blockers.

2 Claims, 4 Drawing Sheets

OTHER PUBLICATIONS

Galizzi et al., "Neuroleptics of the Diphenylbutylpiperidine Series are Potent Calcium Channel Inhibitors," Proc Natl Acad Sci USA (1986) 83: 7513–7517.

Glamkowski, E. et al. (1977). *J of Medicinal Chemistry* 20(11):1485–1489.

Gould et al., "Antischizophrenic Drugs of the Diphenylbutylpiperidine Type Act as Calcium Channel Antagonists," Proc Natl Acad Sci (1983) 80:5122–5125.

Grantham et al., "Fluspirilene Block of N–Type Calcium Current in NGF–Differentiated PC12 Cells," Brit J Phamacol (1994) 111:438–488.

Ito et al., "U–92032, a T–Type $Ca^{2+}$ Channel Blocker and Antioxidant, Reduces Neuronal Ischemic Injuries," Eur J Pharmacol (1994) 257:203–210.

King et al., "Substituted Diphenylbutylpiperidines Bind to a Unique High Affinity Site on the L–Type Calcium Channel," J Biol Chem (1989) 264:5633–5641.

Lee et al., "Cloning and Expression of a Novel Member of the Low Voltage–Activated T–Type Calcium Channel Family," Journal of Neuroscience (1999) 19:1912–1921.

Lehmann et al. (1988). *Archiv der Pharmazie* 321(11):807–812.

McCleskey et al., "Functional Properties of Voltage Dependent Calcium Channels," Curr Topics Membr (1991) 39:295–326.

Miyano, S. et al. (1990). *Chem Pharm Bull* 38(6):1570–1574.

Ohtaka, H. et al. (1987). *Chem Pharm Bull* 35(8):3270–3275.

Ohtaka, H. et al. (1987). *Chem Pharm Bull* 35(10):4117–4123.

Perez–Reyes et al., "Molecular Characterization of a Neuronal Low–Voltage–Activated T–Type Calcium Channel," Nature (1998) 391:896–900.

Prasad, R. et al. (1968). *J of Medicinal Chemistry* 11(6):1144–1150.

Sather et al., "Distinctive Biophysical and Pharmacological Properties of Class A (BI) Calcium Channel $\alpha_1$ Subunits," Neuron (1993) 11:291–303.

Stea et al., "Localization and Functional Properties of a Rat Brain $\alpha_{1A}$ Calcium Channel Reflect Similarities to Neuronal Q–and P–Type Channels," Proc Natl Acad Sci USA (1994) 91:10576–10580.

Stea et al., Handbook of Receptors and Channels (North, R.A. ed. CRC Press 1995) 113–151.

Tytgat, J. et al. (1991). *Brain Research* 549(1):112–117.

Uneyama, H. et al. (1998). *Calcium Ion Modulators,* Sel Pap Satell Symp 13–23.

Vadodaria, D. et al. (1969). *J of Medicinal Chemistry* 12:860–865.

Zikolova, S. et al. (1972). *Tr. Nauchnoizsled Khim–Farm Inst* 8:59–67.

Zikolova, S. et al. (1984). *Tr. Nauchnoizsled Khim–Farm Inst* 14:23–28.

* cited by examiner

PREFERENTIALLY SUBSTITUTED CALCIUM CHANNEL BLOCKERS

This application is a continuation of U.S. Ser. No. 09/476,927 filed Dec. 30, 1999, now U.S. Pat. No. 6,387,897, which is a continuation-in-part of U.S. Ser. No. 09/401,699, filed Sep. 23, 1999 now U.S. Pat. No. 6,294,533, which is a continuation-in-part of U.S. Ser. No. 09/107,037 filed Jun. 30, 1998 and now U.S. Pat. No. 6,011,035. The contents of all applications are incorporated herein by reference.

TECHNICAL FIELD

The invention relates to compounds useful in treating conditions associated with calcium channel function. More specifically, the invention concerns compounds containing substituted or unsubstituted derivatives of 6-membered heterocyclic moieties that are useful in treatment of conditions such as stroke and pain.

BACKGROUND ART

Native calcium channels have been classified by their electrophysiological and pharmacological properties as T, L, N, P and Q types (for reviews see McCleskey, E. W. et al. *Curr Topics Membr* (1991) 39:295–326, and Dunlap, K. et al. *Trends Neurosci* (1995) 18:89–98). T-type (or low voltage-activated) channels describe a broad class of molecules that transiently activate at negative potentials and are highly sensitive to changes in resting potential. The L, N, P and Q-type channels activate at more positive potentials (high voltage activated) and display diverse kinetics and voltage-dependent properties. There is some overlap in biophysical properties of the high voltage-activated channels, consequently pharmacological profiles are useful to further distinguish them. L-type channels are sensitive to dihydropyridine agonists and antagonists, N-type channels are blocked by the *Conus geographus* peptide toxin, ω-conotoxin GVIA, and P-type channels are blocked by the peptide ω-agatoxin IVA from the venom of the funnel web spider, *Agelenopsis aperta*. A fourth type of high voltage-activated calcium channel (Q-type) has been described, although whether the Q- and P-type channels are distinct molecular entities is controversial (Sather, W. A. et al. *Neuron* (1995) 11:291–303; Stea, A. et al. *Proc Natl Acad Sci USA* (1994) 91:10576–10580; Bourinet, E. et al. *Nature Neuroscience* (1999) 2:407–415). Several types of calcium conductances do not fall neatly into any of the above categories and there is variability of properties even within a category suggesting that additional calcium channels subtypes remain to be classified.

Biochemical analyses show that neuronal high voltage activated calcium channels are heterooligomeric complexes consisting of three distinct subunits ($\alpha_1$, $\alpha_2\delta$ and $\beta$) (reviewed by De Waard, M. et al. *Ion Channels* (1997) vol. 4, Narahashi, T. ed. Plenum Press, NY). The $\alpha_1$ subunit is the major pore-forming subunit and contains the voltage sensor and binding sites for calcium channel antagonists. The mainly extracellular $\alpha_2$ is disulfide-linked to the transmembrane $\delta$ subunit and both are derived from the same gene and are proteolytically cleaved in vivo. The $\beta$ subunit is a nonglycosylated, hydrophilic protein with a high affinity of binding to a cytoplasmic region of the $\alpha_1$ subunit. A fourth subunit, $\gamma$, is unique to L-type calcium channels expressed in skeletal muscle T-tubules. The isolation and characterization of $\gamma$-subunit-encoding cDNAs is described in U.S. Pat. No. 5,386,025 which is incorporated herein by reference.

Recently, each of these $\alpha_1$ subtypes has been cloned and expressed, thus permitting more extensive pharmacological studies. These channels have been designated $\alpha_{1A}$-$\alpha_{1I}$ and $\alpha_{1S}$ and correlated with the subtypes set forth above. $\alpha_{1A}$ channels are of the P/Q type; $\alpha_{1B}$ represents N; $\alpha_{1C}$, $\alpha'_{1D}$, $\alpha_{1F}$ and $\alpha_{1S}$ represent L; $\alpha_{1E}$ represents a novel type of calcium conductance, and $\alpha_{1G}$-$\alpha_{1I}$ represent members of the T-type family, reviewed in Stea, A. et al. in Handbook of Receptors and Channels (1994), North, R. A. ed. CRC Press; Perez-Reyes, et al. *Nature* (1998) 391:896–900; Cribbs, L. L. et al. *Circulation Research* (1998) 83:103–109; Lee, J. H. et al. *Journal of Neuroscience* (1999) 19:1912–1921.

Further details concerning the function of N-type channels, which are mainly localized to neurons, have been disclosed, for example, in U.S. Pat. No. 5,623,051, the disclosure of which is incorporated herein by reference. As described, N-type channels possess a site for binding syntaxin, a protein anchored in the presynaptic membrane. Blocking this interaction also blocks the presynaptic response to calcium influx. Thus, compounds that block the interaction between syntaxin and this binding site would be useful in neural protection and analgesia. Such compounds have the added advantage of enhanced specificity for presynaptic calcium channel effects.

U.S. Pat. No. 5,646,149 describes calcium channel antagonists of the formula A-Y-B wherein B contains a piperazine or piperidine ring directly linked to Y. An essential component of these molecules is represented by A, which must be an antioxidant; the piperazine or piperidine itself is said to be important. The exemplified compounds contain a benzhydril substituent, based on known calcium channel blockers (see below). U.S. Pat. No. 5,703,071 discloses compounds said to be useful in treating ischemic diseases. A mandatory portion of the molecule is a tropolone residue; among the substituents permitted are piperazine derivatives, including their benzhydril derivatives. U.S. Pat. No. 5,428,038 discloses compounds which are said to exert a neural protective and antiallergic effect. These compounds are coumarin derivatives which may include derivatives of piperazine and other six-membered heterocycles. A permitted substituent on the heterocycle is diphenylhydroxymethyl. Thus, approaches in the art for various indications which may involve calcium channel blocking activity have employed compounds which incidentally contain piperidine or piperazine moieties substituted with benzhydril but mandate additional substituents to maintain functionality.

Certain compounds containing both benzhydril moieties and piperidine or piperazine are known to be calcium channel antagonists and neuroleptic drugs. For example, Gould, R. J. et al. *Proc Natl Acad Sci USA* (1983) 80:5122–5125 describes antischizophrenic neuroleptic drugs such as lidoflazine, fluspirilene, pimozide, clopimozide, and penfluridol. It has also been shown that fluspirilene binds to sites on L-type calcium channels (King, V. K. et al. *J Biol Chem* (1989) 264:5633–5641) as well as blocking N-type calcium current (Grantham, C. J. et al. *Brit J Pharmacol* (1944) 111:483–488). In addition, Lomerizine, as developed by Kanebo K K, is a known calcium channel blocker; Lomerizine is, however, not specific for N-type channels. A review of publications concerning Lomerizine is found in Dooley, D., *Current Opinion in CPNS Investigational Drugs* (1999) 1:116–125.

The present invention is based on the recognition that the combination of a six-membered heterocyclic ring containing at least one nitrogen said nitrogen coupled through a linker to a benzhydril moiety results in effective calcium channel blocking activity. In some cases enhanced specificity for N-type channels, or decreased specificity for L-type channels is shown. The compounds are useful for treating stroke and pain and other calcium channel-associated disorders, as further described below. By focusing on these moieties, compounds useful in treating indications associated with calcium channel activity are prepared.

DISCLOSURE OF THE INVENTION

The invention relates to compounds useful in treating conditions such as stroke, head trauma, migraine, chronic, neuropathic and acute pain, epilepsy, hypertension, cardiac arrhythmias, and other indications associated with calcium metabolism, including synaptic calcium channel-mediated functions. The compounds of the invention are benzhydril or partly saturated benzhydril derivatives of piperidine or piperazine with substituents which enhance the calcium channel blocking activity of the compounds. Thus, in one aspect, the invention is directed to therapeutic methods that employ compounds of the formula

(1)

wherein Cy represents cyclohexyl;
Y is CH=CHΦ, CHΦ$_2$, Φ or Cy,
X is trivalent straight-chain alkylene (3–10C) or trivalent straight-chain 1-alkenylene (3–10C) optionally substituted by oxo at the C adjacent N when n is 0 and Y is Φ$_2$CH; and is otherwise trivalent straight-chain alkylene (5–10C) or trivalent straight-chain 1-alkenylene (5–10C) optionally substituted by oxo at the C adjacent N;
Z is N, NCO, CHNCOR$^1$ or CHNR$^1$, wherein R$^1$ is alkyl (1–6C); and
n is 0–5;
  wherein each Φ and Cy independently may optionally be substituted by alkyl (1–6C) or by halo, CF$_3$, OCF$_3$, NO$_2$, NR$_2$, OR, SR, COR, COOR, CONR$_2$, NROCR or OOCR where R is H or alkyl (1–4C), or two substituents may form a 5–7 membered ring
  with the proviso that the compounds of formula (1) contain at least one aromatic moiety.

The invention is directed to methods to antagonize calcium channel activity using the compounds of formula (1) and thus to treat associated conditions. It will be noted that the conditions may be associated with abnormal calcium channel activity, or the subject may have normal calcium channel function which nevertheless results in an undesirable physical or metabolic state. In another aspect, the invention is directed to pharmaceutical compositions containing these compounds.

The invention is also directed to combinatorial libraries containing the compounds of formula (1) and to methods to screen these libraries for members containing particularly potent calcium channel blocking activity or for members that antagonize one type of such channels specifically.

MODES OF CARRYING OUT THE INVENTION

Figure 1A:
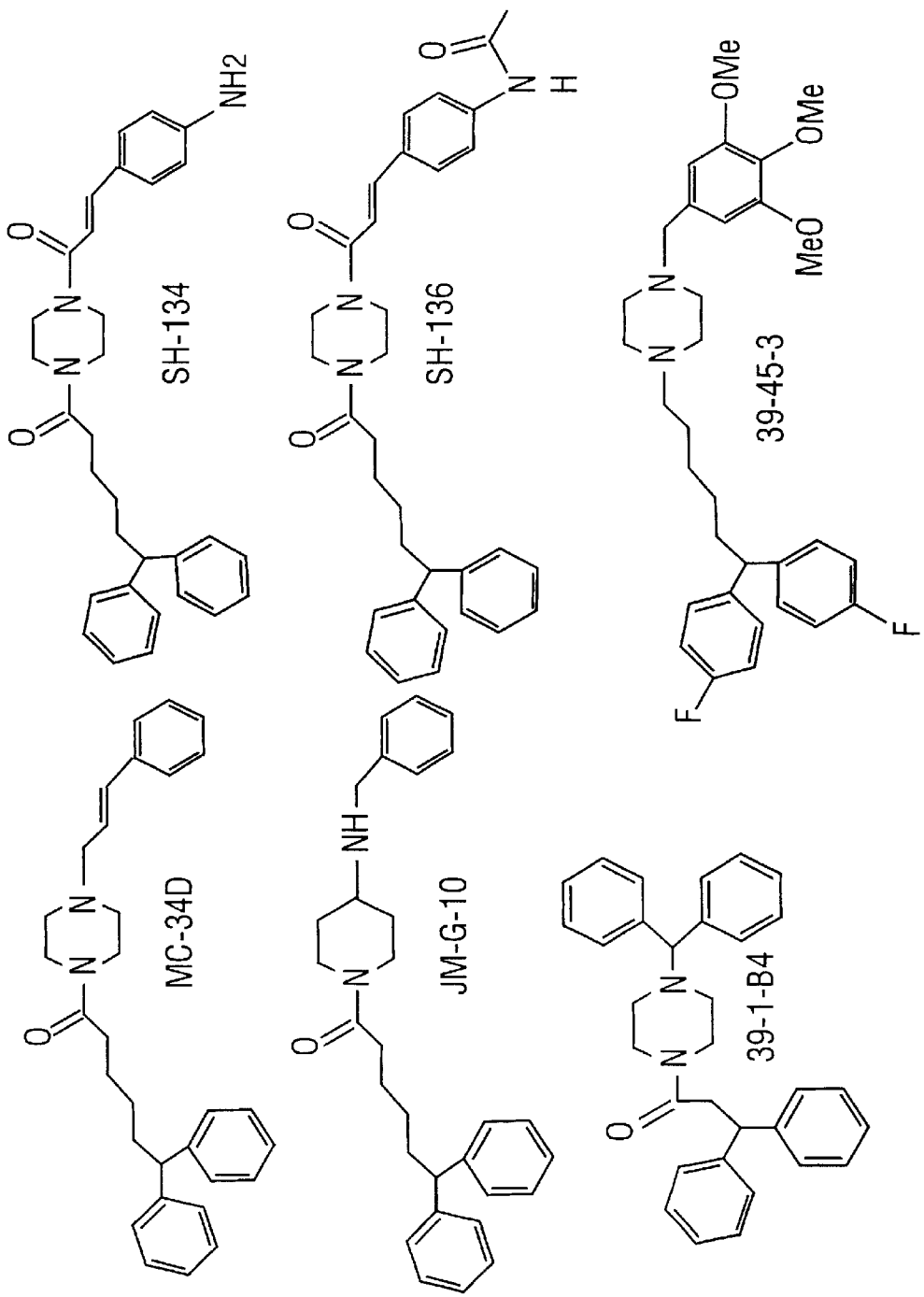
FIGS. 1A and 1B shows a comparison of certain preferred embodiments of the compounds of the invention to the known compound Lomerizine.

The compounds of formula (1), useful in the methods of the invention, exert their desirable effects through their ability to antagonize the activity of calcium channels. This makes them useful for treatment of certain conditions. Among such conditions are stroke, epilepsy, head trauma, migraine and chronic, neuropathic and acute pain. Calcium flux is also implicated in other neurological disorders such as schizophrenia, anxiety, depression, other psychoses, and certain degenerative disorders. Other treatable conditions include cardiovascular conditions such as hypertension and cardiac arrhythmias.

While the compounds of formula (1) generally have this activity, the availability of a multiplicity of calcium channel blockers permits a nuanced selection of compounds for particular disorders. Thus, the availability of this class of compounds provides not only a genus of general utility in indications that are affected by excessive calcium channel activity, but also provides a large number of compounds which can be mined and manipulated for specific interaction with particular forms of calcium channels. The availability of recombinantly produced calcium channels of the $\alpha_{1A}$-$\alpha_{1I}$ and $\alpha_{1S}$ types set forth above, facilitates this selection process. Dubel, S. J. et al. *Proc Natl Acad Sci USA* (1992) 89:5058–5062; Fujita, Y. et al. *Neuron* (1993) 10:585–598; Mikami, A. et al. *Nature* (1989) 340:230–233; Mori, Y. et al. *Nature* (1991) 350:398–402; Snutch, T. P. et al. *Neuron* (1991) 7:45–57; Soong, T. W. et al. *Science* (1993) 260:1133–1136; Tomlinson, W. J. et al. *Neuropharmacology* (1993) 32:1117–1126; Williams, M. E. et al. *Neuron* (1992) 8:71–84; Williams, M. E. et al. *Science* (1992) 257:389–395; Perez-Reyes, et al. *Nature* (1998) 391:896–900; Cribbs, L. L. et al. *Circulation Research* (1998) 83:103–109; Lee, J. H. et al. *Journal of Neuroscience* (1999) 19:1912–1921.

Thus, while it is known that calcium channel activity is involved in a multiplicity of disorders, the types of channels associated with particular conditions is the subject of ongoing data collection. For example, the association of N-type channels in conditions associated with neural transmission would indicate that compounds of the invention which target N-type receptors are most useful in these conditions. Many of the members of the genus of compounds of formula (1) exhibit high affinity for N-type channels; other members of the genus may preferentially target other channels.

There are two distinguishable types of calcium channel inhibition. The first, designated "open channel blockage," is conveniently demonstrated when displayed calcium channels are maintained at an artificially negative resting potential of about −100 mV (as distinguished from the typical endogenous resting maintained potential of about −70 mV). When the displayed channels are abruptly depolarized under these conditions, calcium ions are caused to flow through the channel and exhibit a peak current flow which then decays. Open channel blocking inhibitors diminish the current exhibited at the peak flow and can also accelerate the rate of current decay.

This type of inhibition is distinguished from a second type of block, referred to herein as "inactivation inhibition." When maintained at less negative resting potentials, such as the physiologically important potential of −70 mV, a certain percentage of the channels may undergo conformational change, rendering them incapable of being activated—i.e., opened—by the abrupt depolarization. Thus, the peak current due to calcium ion flow will be diminished not because the open channel is blocked, but because some of the channels are unavailable for opening (inactivated). "Inactivation" type inhibitors increase the percentage of receptors that are in an inactived state.

Synthesis

The compounds of the invention may be synthesized using conventional methods. Illustrative of such methods are Schemes 1 and 2:

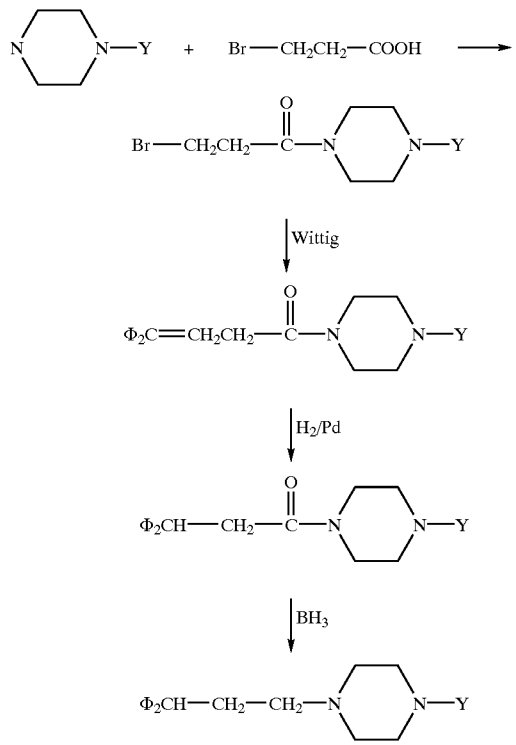

Alternatively, a carboxylic acid containing the benzhydril (or ΦCyCH or Cy₂CH) moiety can first be synthesized and then reacted with the piperazine (or piperidine) moiety and subsequently reduced. To synthesize the desired acid, an ω-bromo carboxylic acid is refluxed with, in the case of benzhydril, triphenylphosphine in the presence of methyl nitrile and then treated with lithium hexamethyldisilazide in a solvent such as THF. The resulting unsaturated carboxylic acid containing the two phenyl substituents is then reduced as shown in Scheme 1 with hydrogen on a palladium catalyst and then reacted with derivatized piperazine (or piperidine) to form the amide. The amide can then be reduced as shown above.

Scheme 2 (Z is CHNR¹)

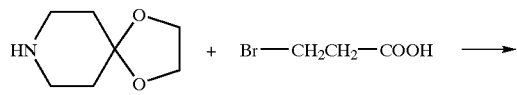

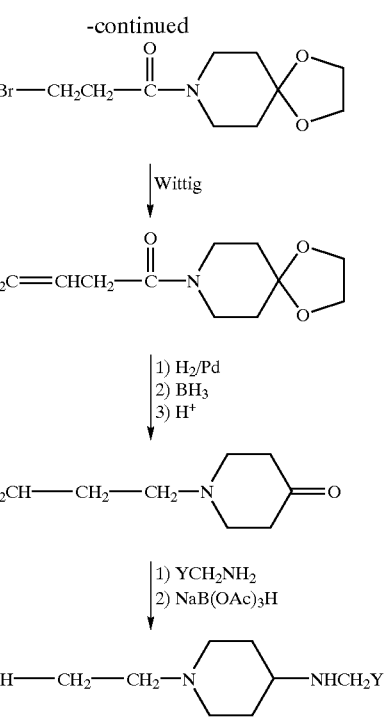

Preferred Embodiments

The compounds of formula (1) are defined as shown in terms of the embodiments of their various substituents:

Particularly preferred embodiments of the compounds of formula (1) are those wherein X is coupled to two phenyl groups. Less preferred are instances where X is coupled to one phenyl and one cyclohexyl. Least preferred are those instances wherein X is coupled to two cyclohexyl groups.

As defined above, X may be a trivalent straight-chain alkylene of 5–10C optionally substituted with oxo at the position adjacent the piperidine or piperazine ring nitrogen. Preferably, the alkylene chain is 5–8C, more preferably 5–7C, and even more preferably 5–6C. Substitution with oxo is preferred only when the length of the alkylene chain is 6–10C. In addition, X may be a straight-chain 1-alkenylene (5–10C) wherein the π-bond is in the position distal to the piperidine or pyrimidine ring nitrogen. Under these circumstances, the two cyclic moieties are accommodated by the alkenylene chain by virtue of the alkenylene chain as a vinyl substituent to each cyclic moiety. In addition, when n is 0 and Y is Φ₂CH, the embodiment of X described above may also be shorter and may contain 3–10C.

Preferred embodiments of Z are N, NCO and CHNR¹ where R¹ is preferably H but may also be alkyl (1–6C), preferably 1–4C, more preferably 1–2C, and even more preferably methyl (or H).

Preferred embodiments for n are 0–4, more preferably 1–2.

Any of the phenyl or cyclohexyl moieties contained in the compounds of formula (1) may be substituted, as noted above. Preferred substituents include halo, especially fluoro, NO₂, alkyl (1–6C), preferably methyl, OR, preferably methoxy, NR₂, preferably dimethylamino, diethylamino, methylamino or ethylamino, acetamido, CF₃, OCF₃ and the like. Two substituted positions may also form a ring. Preferably, where the cyclic moieties coupled to X are both phenyl, the phenyl groups are identically substituted. Where one such moiety is phenyl and the other is cyclohexyl, the presence of a substituent on the phenyl moiety and an unsubstituted cyclohexyl moiety are preferred. It is believed that halogenation of the compounds of the invention is helpful in modulating the in vivo half-life, and it may be particularly advantageous to include halogen substituents, such as fluoro substitutions on any phenyl moieties.

Figure 1B:
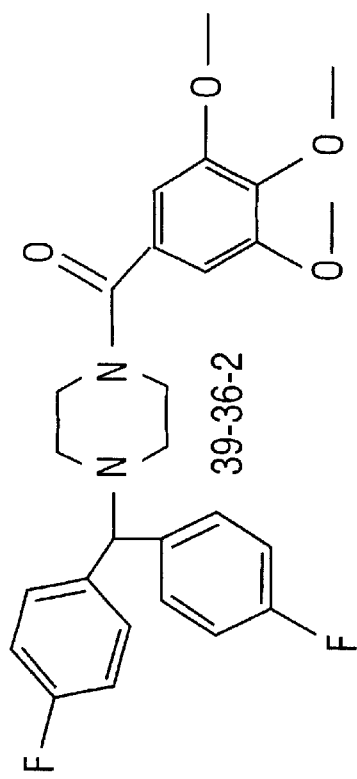
Figure 1B:
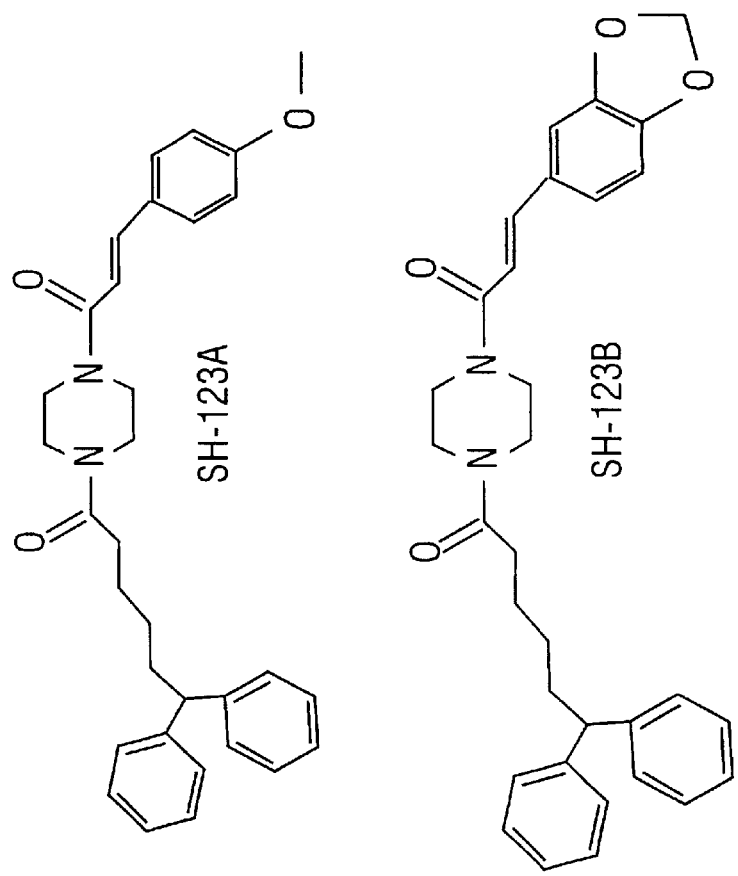

Particularly preferred are compounds MC-34D, JM-G-10, 39-1-B4, and 39-45-3 shown in FIG. 1 and variously substituted forms thereof.

Thus, also preferred are forms of these enumerated compounds which contain different substituents on the phenyl or cyclohexyl moieties from those shown. Thus, also preferred are compounds having the general formula of MC-34D wherein the two phenyl moieties attached to X contain fluoro in the para position. Alternative substitutions are as shown below where Φ1 and Φ2 indicate the 2 phenyl groups attached to X (the numbers being arbitrarily chosen as these phenyl groups are equivalent) and Φ3 represents phenyl group contained in Y. In addition, also preferred are embodiments as set forth herein where Z of MC-34D is NCO or wherein X is —CH(CH$_2$)—$_5$.

| Φ1 | Φ2 | Φ3 |
|---|---|---|
| 2,4-dimethyl | 2,4, dimethyl | 4-F |
| 4-methoxy | 3-chloro | 4-methyl |
| 2,4,6 trimethyl amino | 2,4,6 trimethyl amino | — |
| 4-F | 4-F | 4-F |
| 4-F | 4-F | 4-methoxy |
| 4-F | 4-F | 3,4-OCH$_2$O— |

Similarly, JM-G-10 with substituents on the phenyl groups and cyclohexyl group may be employed in the methods of the invention, preferred embodiments also include those wherein X is —CH(CH$_2$)—$_5$. Suitable substitutions are shown below:

| Φ1 | Φ2 | Cy |
|---|---|---|
| 4-F | 4-F | — |
| 2,4-dimethoxy | 4-methyl | 3,5-diethyl |
| 3,5-diamino | 3;5-diamino | 4-F |

Alternatively substituted compounds of formula 39-1-B4 are also included within the preferred embodiments of the invention. In the table below, Φ1 and Φ2 represent the two equivalent phenyl groups coupled to X and Φ3 and Φ4 represent the two equivalent phenyl groups included in Y. Forms of 39-1-B4 wherein the carbonyl group in X is reduced to methylene are also preferred, including those with the substituents shown below.

| Φ1 | Φ2 | Φ3 | Φ4 |
|---|---|---|---|
| 4-F | 4-F | — | — |
| 3,4-CH$_2$CH$_2$CH$_2$— | 3,4-CH$_2$CH$_2$CH$_2$— | 4-F | 4-F |
| 2,6-dimethoxy 4-COOH | 3,5,diamino 4-COOH | 3,5,diamino 3,5 dichloro | 2,6,dimethoxy 3,5-dichloro |

Similarly, various alternative substitution patterns on compound 39-45-3 may be employed. Included are those embodiments where a carbonyl is present adjacent the piperazine in the substituent X. Also included are analogs where n=0. Particularly preferred are embodiments where two substituents on the phenyl group contained in Y form a ring, particularly a 5-membered ring. Thus, preferred substitution patterns are those set forth below where Φ1 and Φ2 represent the two equivalent phenyl groups attached to X and Φ3 represents the phenyl group contained in Y.

| Φ1 | Φ2 | Φ3 |
|---|---|---|
| 4-F | 4-F | 3,4,5-trimethoxy |
| 4-F | 4-F | 3,4,-CH$_2$CH$_2$—CH$_2$— |
| 4-F | 4-F | 3,4,5-tri trifluro-methyl |
| 4-F | 4-F | 3,4,-OCH$_2$O— |
| 2,4,6 trimethoxy | — | 4-F |
| 3,5-diethoxy | 3,5-diethoxy | 3,5-diethoxy |
| 4-F | 4-F | 3,5-detrifluoromethyl |
| 4-F | 4-F | 5-OCF$_3$ |
| 4-f | 4-F | 3,4 dimethyl |
| 4-F | 4-F | 3-methoxy |
| 4-F | 4-F | 4-F |
| 4-F | 4-F | 3-methyl |
| 4-F | 4-F | 2-methoxy |
| 4-F | 4-F | 4-acetyl |

The pattern of substitution will influence the strength of calcium channel blocking ability as well as specificity.

Where the structure permits, invention compounds may also be supplied as pharmaceutically acceptable salts. Pharmaceutically acceptable salts include the acid addition salts which can be formed from inorganic acids such as hydrochloric, sulfuric, and phosphoric acid or from organic acids such as acetic, propionic, glutamic, glutaric, as well as acid ion-exchange resins.

Libraries and Screening

The compounds of the invention can be synthesized individually using methods known in the art per se, or as members of a combinatorial library.

Synthesis of combinatorial libraries is now commonplace in the art. Suitable descriptions of such syntheses are found, for example, in Wentworth, Jr., P. et al. *Current Opinion in Biol* (1993) 9:109–115; Salemme, F. R. et al. *Structure* (1997) 5:319–324. The libraries contain compounds with various substitutents and various degrees of unsaturation, as well as different chain lengths. The libraries, which contain, as few as 10, but typically several hundred members to several thousand members, may then be screened for compounds which are particularly effective against a specific subtype of calcium channel, i.e., the N-type channel. In addition, using standard screening protocols, the libraries, may be screened for compounds which block additional channels or receptors such as sodium channels, potassium channels and the like.

The libraries useful as sources of candidate compounds comprise compounds of the formula

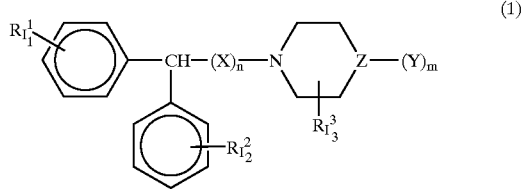

(1)

wherein m is 0, 1 or 2;
wherein when m is 0, Z is O, when m is 1, Z is N, and when m is 2, Z is C;
Y is H, OH, NH$_2$, or an organic moiety of 1–20C, optionally additionally containing 1–8 heteroatoms selected from the group consisting of N, P, O, S and halo;

each $l^1$ and $l^2$ is independently 0–5;
$l^3$ is 0 or 1;
each of $R^1$, $R^2$ and $R^3$ is independently alkyl (1–6C), aryl (6–10C) or arylalkyl (7–16C) optionally containing 1–4 heteroatoms selected from the group consisting of halo, N, P, O, and S or each of $R^1$ and $R^2$ may independently be halo, COOR, CONR$_2$, CF$_3$, CN or NO$_2$, wherein R is H or lower alkyl (1–4C) or alkyl (1–6C);
n is 0 or 1; and
X is a linker.

Methods of performing these screening functions are well known in the art. Typically, the receptor to be targeted is expressed at the surface of a recombinant host cell such as human embryonic kidney cells. The ability of the members of the library to bind the channel to be tested is measured, for example, by the ability of the compound in the library to displace a labeled binding ligand such as the ligand normally associated with the channel or an antibody to the channel. More typically, ability to antagonize the receptor is measured in the presence of calcium ion and the ability of the compound to interfere with the signal generated is measured using standard techniques.

In more detail, one method involves the binding of radiolabeled agents that interact with the calcium channel and subsequent analysis of equilibrium binding measurements including, but not limited to, on rates, off rates, $K_d$ values and competitive binding by other molecules. Another method involves the screening for the effects of compounds by electrophysiological assay whereby individual cells are impaled with a microelectrode and currents through the calcium channel are recorded before and after application of the compound of interest. Another method, high-throughput spectrophotometric assay, utilizes loading of the cell lines with a fluorescent dye sensitive to intracellular calcium concentration and subsequent examination of the effects of compounds on the ability of depolarization by potassium chloride or other means to alter intracellular calcium levels.

As described above, a more definitive assay can be used to distinguish inhibitors of calcium flow which operate as open channel blockers, as opposed to those that operate by promoting inactivation of the channel. The methods to distinguish these types of inhibition are more particularly described in the examples below. In general, open-channel blockers are assessed by measuring the level of peak current when depolarization is imposed on a background resting potential of about −100 mV in the presence and absence of the candidate compound. Successful open-channel blockers will reduce the peak current observed and may accelerate the decay of this current. Compounds that are inactivated channel blockers are generally determined by their ability to shift the voltage dependence of inactivation towards more negative potentials. This is also reflected in their ability to reduce peak currents at more depolarized holding potentials (e.g., −70 mV) and at higher frequencies of stimulation, e.g., 0.2 Hz vs. 0.03 Hz.

Utility and Administration

For use as treatment of human and animal subjects, the compounds of the invention can be formulated as pharmaceutical or veterinary compositions. Depending on the subject to be treated, the mode of administration, and the type of treatment desired—e.g., prevention, prophylaxis, therapy; the compounds are formulated in ways consonant with these parameters. A summary of such techniques is found in Remington's *Pharmaceutical Sciences*, latest edition, Mack Publishing Co., Easton, Pa., incorporated herein by reference.

In general, for use in treatment, the compounds of formula (1) maybe used alone, as mixtures of two or more compounds of formula (1) or in combination with other pharmaceuticals. Depending on the mode of administration, the compounds will be formulated into suitable compositions to permit facile delivery.

Formulations may be prepared in a manner suitable for systemic administration or topical or local administration. Systemic formulations include those designed for injection (e.g., intramuscular, intravenous or subcutaneous injection) or may be prepared for transdermal, transmucosal, or oral administration. The formulation will generally include a diluent as well as, in some cases, adjuvants, buffers, preservatives and the like. The compounds can be administered also in liposomal compositions or as microemulsions.

For injection, formulations can be prepared in conventional forms as liquid solutions or suspensions or as solid forms suitable for solution or suspension in liquid prior to injection or as emulsions. Suitable excipients include, for example, water, saline, dextrose, glycerol and the like. Such compositions may also contain amounts of nontoxic auxiliary substances such as wetting or emulsifying agents, pH buffering agents and the like, such as, for example, sodium acetate, sorbitan monolaurate, and so forth.

Various sustained release systems for drugs have also been devised. See, for example, U.S. Pat. No. 5,624,677.

Systemic administration may also include relatively non-invasive methods such as the use of suppositories, transdermal patches, transmucosal delivery and intranasal administration. Oral administration is also suitable for compounds of the invention. Suitable forms include syrups, capsules, tablets, as in understood in the art.

For administration to animal or human subjects, the dosage of the compounds of the invention is typically 0.1–15 mg/kg, preferably 0.1–1 mg/kg. However, dosage levels are highly dependent on the nature of the condition, the condition of the patient, the judgment of the practitioner, and the frequency and mode of administration.

The following examples are intended to illustrate but not to limit the invention.

EXAMPLE 1

Assessment of Calcium Channel Blocking Activity

Antagonist activity was measured using whole cell patch recordings on human embryonic kidney cells either stably or transiently expressing rat $\alpha_{1B}+\alpha_{2b}+\beta_{1b}$ channels (N-type channels) with 5 mM barium as a charge carrier.

For transient expression, host cells, such as human embryonic kidney cells, HEK 293 (ATCC# CRL 1573) were grown in standard DMEM medium supplemented with 2 mM glutamine and 10% fetal bovine serum. HEK 293 cells were transfected by a standard calcium-phosphate-DNA coprecipitation method using the rat $\alpha_{1B}+\beta_{1b}+\alpha_2\delta$ N-type calcium channel subunits in a vertebrate expression vector (for example, see *Current Protocols in Molecular Biology*).

After an incubation period of from 24 to 72 hrs the culture medium was removed and replaced with external recording solution (see below). Whole cell patch clamp experiments were performed using an Axopatch 200B amplifier (Axon Instruments, Burlingame, Calif.) linked to an IBM compatible personal computer equipped with pCLAMP software. Borosilicate glass patch pipettes (Sutter Instrument Co., Novato, Calif.) were polished (Microforge, Narishige, Japan) to a resistance of about 4 MΩ when filled with cesium methanesulfonate internal solution (composition in MM: 109 CsCH$_3$SO$_4$, 4 MgCl$_2$, 9 EGTA, 9 HEPES, pH 7.2).

Cells were bathed in 5 mM $Ba^{++}$ (in mM: 5 $BaCl_2$, 1 $MgCl_2$, 10 HEPES, 40 tetraethylammonium chloride, 10 glucose, 87.5 CsCl pH 7.2). Current data shown were elicited by a train of 100 ms test pulses at 0.066 Hz from −100 mV and/or −80 mV to various potentials (min. −20 mV, max. +30 mV). Drugs were perfused directly into the vicinity of the cells using a microperfusion system.

Normalized dose-response curves were fit (Sigmaplot 4.0, SPSS Inc., Chicago, Ill.) by the Hill equation to determine $IC_{50}$ values. Steady-state inactivation curves were plotted as the normalized test pulse amplitude following 5 s inactivating prepulses at +10 mV increments. Inactivation curves were fit (Sigmaplot 4.0) with the Boltzman equation, $I_{peak}$ (normalized)$=1/(1+\exp((V-V_h)z/25.6))$, where V and $V_h$ are the conditioning and half inactivation potentials, respectively, and z is the slope factor.

EXAMPLE 2

Synthesis of Illustrative Compounds of Formula (1)

A. Synthesis of 6,6-Diphenyl Hexanoic Acid.

6-Bromohexanoic acid (7.08 g, 36.3 mmole) and triphenylphosphine (10 g, 38.2 mmole) were mixed in dry $CH_3CN$ (40 ml), heated to reflux overnight and allowed to cool to RT. The solution was concentrated under reduced pressure to give a viscous gel. Approximately 75 ml of THF was added to the reaction mixture and the walls of the flask were scratched with a spatula to start crystallization. The resulting solid was filtered under vacuum, washed with THF and dried under reduced pressure and used without further purification.

This product (1.5 g) was suspended in dry THF (10 ml) and the flask purged with $N_2$ and cooled to −78° C. To the stirred reaction was added lithium hexamethyldisilazide (LiHMDS) (10 ml, 1 M in THF). The yellow solution was stirred at −78° C. for 1 h over which time the reaction darkened slightly. The cooling bath was removed and the reaction allowed to warm to RT. The reaction was kept at RT for 1 h during which time the solution turned a dark red color and most of the solids went into solution. Benzophenone (0.54 g in 3 ml THF) was added to the reaction and allowed to react overnight. The yellow solution was concentrated under reduced pressure to give a yellow solid. The resulting solid was partitioned between ether and 10% HCl. The organic layer was washed with water (2×) and extracted with 10% NaOH (3×). The combined aqueous base fraction was acidified with conc. HCl to a pH of 4. The water layer was extracted with ether (3×) and the combined organic fractions dried over $Na_2SO_4$.

The ether was evaporated to dryness under reduced pressure to give a colorless oil which crystallized on standing to give a waxy solid, 6,6-diphenyl hex-5-enoic acid, which was dissolved in 30 ml MeOH and mixed with 5% Pd—C and placed in a Parr hydrogenator. The reaction vessel was purged with hydrogen and pressurized to 60 PSIG and reacted at RT for 4 h. The reaction mixture was sampled and analyzed by TLC. If the TLC when stained with $KMnO_4$ showed a positive test for alkenes the reaction mixture was resubjected to the reaction conditions. The solution was then filtered through a plug of celite and the methanol filtrate containing 6,6-diphenyl hexanoic acid was concentrated under vacuum.

B. Reaction with Substituted Piperazine.

6,6-Diphenylhexanoic acid (0.4 mmoles) was mixed with the desired substituted piperazine (0.35 mmoles) in dry THF (7 ml). EDC (0.5 mmoles) and DMAP (cat) were added and the mixture heated to 40° C. with shaking overnight. The reaction was diluted with ethyl acetate and washed with water (4×) and 10% NaOH (3×) and dried over sodium sulfate and evaporated to dryness. The resulting residue was purified by column chromatography (silica gel, 1:1 hexane:EtOAc), and the products were characterized by HPLC-MS.

Piperazines used in the foregoing procedure include phenylpiperazine, benzylpiperazine, benzhydrilpiperazine, and piperazine substituted at the 1-position with Φ—CH═$CH_2$—.

The resulting compounds contain a carbonyl adjacent to the ring nitrogen of piperazine. These compounds are of formula (1) and exhibit calcium channel blocking activity.

C. Reduction of CO.

The compounds prepared in paragraph B were dissolved in dry THF (5 ml) and reacted with $LiAlH_4$ (1 M in THF) and allowed to react for 6 h. The reactions were quenched with EtOAc (15 ml) and extracted with water (5×) 10% NaOH (10×), brine (1×), dried over sodium sulfate and concentrated under reduced pressure. Most of the products at this stage were >80% pure. Those <80% were purified for running a short column (silica gel, 1:1 hex:EtOAc).

EXAMPLE 3

Preparation of Compounds of Formula (1) from Benzhydrilpiperazine Derivatives N-(Diphenylmethyl)piperazine (0.5 mmole) was dissolved in dry THF (10 ml). To each reaction flask was added powdered $K_2CO_3$ and acid chloride of the formula Y—CO—Cl (0.7 mmole). The reaction was stirred at RT for 2 h and quenched with 105 NaOH (10 ml) and extracted with EtOAc (10 ml). The organic layer was washed with 10% NaOH (4×) and dried over sodium sulfate, concentrated, and purified by column chromatography (silica gel, 1:1 hex:EtOAc) to give the desired amide. Acyl halides used in this procedure included cyclohexyl COCl, ΦCOCl and ΦCH═CHCOCl.

To reduce the resulting amide, the above product was dissolved in dry THF (5 ml) and reacted with $LiAlH_4$ (1 M in THF) and allowed to react for 6 h. The reaction was quenched with EtOAc (15 ml) and extracted with water (5×) 10% NaOH (10×), brine (1×), dried over sodium sulfate and concentrated under reduced pressure. Most of the products at this stage were >80% pure. Those <80% were purified for running a short column (silica gel, 1:1 hex:EtOAc).

EXAMPLE 4

Channel Blocking Activities of Various Invention Compounds

Using the procedure set forth in Example 1, various compounds of the invention were tested for their ability to block N-type calcium channels. The results are shown in the table below where $IC_{50}$ is given in μM (micromolar).

| X coupled to | X | Z | n | Y | $IC_{50}$ |
|---|---|---|---|---|---|
| Φ, Φ | $CHCH_2$ | CHNH | 1 | Φ | ±3 |
| Φ, Φ | $CH(CH_2)_2$ | CHNH | 1 | Φ | 2 |
| Φ, Φ | $CHCH_2$ | CHNH | 1 | Cy | 3–4 |
| Φ, Φ | $CH(CH_2)_2$ | CHNH | 1 | Cy | 2–3 |

-continued

| X coupled to | X | Z | n | Y | IC$_{50}$ |
|---|---|---|---|---|---|
| φ, φ | CH(CH$_2$)$_4$CO | CHNH | 1 | Cy | 0.75 |
| φ, φ | C=CH(CH$_2$)$_2$ | N | 1 | Cy | 5.2 |
| φ, Cy | CH(CH$_2$)$_5$ | N | 1 | CH=CHφ | 5.9 |
| φ, Cy | CH(CH$_2$)$_4$CO | N | 1 | CH=CHφ | 3.9 |
| φ, Cy | CH(CH$_2$)$_5$CO | N | 1 | CH=CHφ | 3.2 |
| φ, Cy | CH(CH$_2$)$_5$CO | N | 0 | CHφ$_2$ | 10.2 |
| φ, Cy | CH(CH$_2$)$_5$CO | N | 1 | CH=CHφ | 12.2 |
| φ, Cy | CH(CH$_2$)$_6$ | N | 1 | Cy | 7.2 |
| φ, Cy | CHCH$_2$ | N | 1 | Cy | 20.2 |
| φ, Cy | CHCO | N | 1 | φ | 14.2 |
| φ, Cy | CHCO | N | 1 | CH=CHφ | 5.9 |
| φ, Cy | CHCH$_2$ | N | 1 | φ | ±5 |
| φ, Cy | CH(CH$_2$)$_5$ | N | 2 | φ | 3.1 |
| φ, Cy | CHCO | N | 1 | CH=CHφ | ±5 |
| φ, Cy | CHCH$_2$ | N | 1 | CH=CHφ | 10.6 |
| φ, Cy | CHCH$_2$ | N | 1 | CH=CHφ | ±5 |
| φ, Cy | CHCO | N | 1 | φ | 20 |
| φ, Cy | CHCO | N | 1 | CHφ$_2$ | 35 |
| φ, Cy | CHCH$_2$ | N | 1 | CHφ$_2$ | 20 |

EXAMPLE 5

Additional Methods

The methods of Examples 1 and 2 were followed with slight modifications as will be apparent from the description below.

A. Transformation of HEK Cells:

N-type calcium channel blocking activity was assayed in human embryonic kidney cells, HEK 293, stably transfected with the rat brain N-type calcium channel subunits ($\alpha_{1B}$+$\alpha_{2\delta}$+$\beta_{1b}$ cDNA subunits). Alternatively, N-type calcium channels ($\alpha_{1B}$+$\alpha_{2\delta}$+$\beta_{1b}$ cDNA subunits), L-type channels ($\alpha_{1C}$+$\alpha_{2\delta}$+$\beta_{1b}$ cDNA subunits) and P/Q-type channels ($\alpha_{1A}$+$\alpha_{2\delta}$+$\beta_{1b}$ cDNA subunits) were transiently expressed in HEK 293 cells. Briefly, cells were cultured in Dulbecco's modified eagle medium (DMEM) supplemented with 10% fetal bovine serum, 200 U/ml penicillin and 0.2 mg/ml streptomycin at 37° C. with 5% CO$_2$. At 85% confluency cells were split with 0.25% trypsin/1 mM EDTA and plated at 10% confluency on glass coverslips. At 12 hours the medium was replaced and the cells transiently transfected using a standard calcium phosphate protocol and the appropriate calcium channel cDNAs. Fresh DMEM was supplied and the cells transferred to 28° C./5% CO$_2$. Cells were incubated for 1 to 2 days to whole cell recording.

B. Measurement of Inhibition:

Whole cell patch clamp experiments were performed using an Axopatch 200B amplifier (Axon Instruments, Burlingame, Calif.) linked to a personal computer equipped with pCLAMP software. The external and internal recording solutions contained, respectively, 5 mM BaCl$_2$, 1 mM MgCl$_2$, 10 mM HEPES, 40 mM TEACl, 10 mM glucose, 87.5 mM CsCl (pH 7.2) and 108 mM CsMS, 4 mM MgCl$_2$, 9 mM EGTA, 9 mM HEPES (pH 7.2). Currents were typically elicited from a holding potential of −80 mV to +10 mV using Clampex software (Axon Instruments). Typically, currents were first elicited with low frequency stimulation (0.03 Hz) and allowed to stabilize prior to application of the compounds. The compounds were then applied during the low frequency pulse trains for two to three minutes to assess tonic block, and subsequently the pulse frequency was increased to 0.2 Hz to assess frequency dependent block. Data were analyzed using Clampfit (Axon Instruments) and SigmaPlot 4.0 (Jandel Scientific).

Specific data obtained for N-type channels are shown in Table 1 below. As indicated by the data in Table 1, the most potent inhibitors at higher frequencies were MC-34D, JM-G-10, 39-1-B4 and 39-45-3 shown in FIG. 1. However, all of the compounds tested appeared to be reasonably good blockers at this frequency.

TABLE 1

|  | % Block (100 nM) | | Estimated IC$_{50}$ ($\mu$M) | |
|---|---|---|---|---|
| $\alpha_{1B}$ (N-type) | 0.03 Hz | 0.2 Hz | 0.03 Hz | 0.2 Hz |
| MC-34D | 47 | 73 | 0.12 | 0.05 |
| JM-G-10 | 38 | 63 | 0.17 | 0.06 |
| 39-1-B4 | 34 | 72 | 0.2 | 0.04 |
| SH-123A | 19 | 55 | 0.47 | 0.09 |
| SH-123B | 9 | 45 | 1.27 | 0.13 |
| SH-134 | 20 | 41 | 0.44 | 0.15 |
| SH-136 | 14 | 44 | 0.63 | 0.14 |
| 39-45-3 | 50 | 79 | 0.1 | 0.03 |
| 39-36-1 Lomerizine | 24 | 54 | 0.39 | 0.09 |
| 39-36-2 | 29 | 60 | 0.32 | 0.07 |

Tables 2 and 3 show the results of similar experiments conducted with P/Q-type and L-type channels expressed in HEK 293 cells. In general, the IC$_{50}$ values for MC-34D, JM-G-10, 39-1-B4 and 39-45-3 were higher than those exhibited with respect to N-type channels.

TABLE 2

|  | % Block (100 nM) | | Estimated IC$_{50}$ ($\mu$M) | |
|---|---|---|---|---|
| $\alpha_{1A}$ (P/Q-type) | 0.03 Hz | 0.2 Hz | 0.03 Hz | 0.2 Hz |
| MC-34D | 31 | 56 | 0.35 | 0.08 |
| JM-G-10 | 28 | 62 | 0.3 | 0.07 |
| 39-1-B4 | 31 | 52 | 0.65 | 0.12 |
| SH-123A | 29 | 61 | 0.26 | 0.07 |
| SH-123B | 16 | 44 | 0.55 | 0.13 |
| SH-134 | 20 | 45 | 0.45 | 0.12 |
| SH-136 | 18 | 42 | 0.52 | 0.15 |
| 39-45-3 | 27 | 58 | 0.41 | 0.09 |
| 39-36-1 Lomerizine | 25 | 57 | 0.46 | 0.07 |
| 39-36-2 | 35 | 52 | 0.31 | 0.11 |

TABLE 3

|  | % Block (100 nM) | | Estimated IC$_{50}$ ($\mu$M) | |
|---|---|---|---|---|
| $\alpha_{1C}$ (L-type) | 0.03 Hz | 0.2 Hz | 0.03 Hz | 0.2 Hz |
| MC-34D | 14 | 24 | 0.63 | 0.39 |
| JM-G-10 | 7 | 15 | 1.17 | 0.3 |
| 39-1-B4 | 19 | 29 | 0.5 | 0.3 |
| SH-123A | 21 | 37 | 0.62 | 0.25 |
| SH-123B | 8 | 14 | 2.06 | 0.74 |
| SH-134 | 11 | 21 | 1.6 | 0.83 |
| SH-136 | 4 | 8 | 2.8 | 1.4 |
| 39-45-3 | 15 | 26 | 0.74 | 0.37 |
| 39-36-1 Lomerizine | 26 | 44 | 0.29 | 0.15 |
| 39-36-2 | 11 | 22 | 2.1 | 0.4 |

These data are summarized in Table 4 which show the ratio of IC$_{50}$ values for P:N and L:N channels. As shown, with respect to specificity for L-type channels in particular, the four compounds mentioned above show much higher affinity for N-type and P/Q-type versus L-type channels.

TABLE 4

| 0.2 Hz | N | P/Q | L | P:N | L:N |
|---|---|---|---|---|---|
| MC-34D | 0.05 | 0.08 | 0.39 | 1.6:1 | 8:1 |
| JM-G-10 | 0.06 | 0.07 | 0.3 | 1.2:1 | 5:1 |
| 39-1-B4 | 0.04 | 0.12 | 0.3 | 3:1 | 8:1 |
| SH-123A | 0.09 | 0.07 | 0.25 | 0.8:1 | 3:1 |
| SH-123B | 0.13 | 0.13 | 0.74 | 1:1 | 6:1 |
| SH-134 | 0.15 | 0.12 | 0.83 | 0.8:1 | 6:1 |
| SH-136 | 0.14 | 0.15 | 1.4 | 1.1:1 | 10:1 |
| 39-45-3 | 0.03 | 0.09 | 0.37 | 3:1 | 12:1 |
| 39-36-1 Lomerizine | 0.09 | 0.07 | 0.15 | 0.8:1 | 1.7:1 |
| 39-36-2 | 0.07 | 0.11 | 0.4 | 1.6:1 | 5.7:1 |

Figure 2:
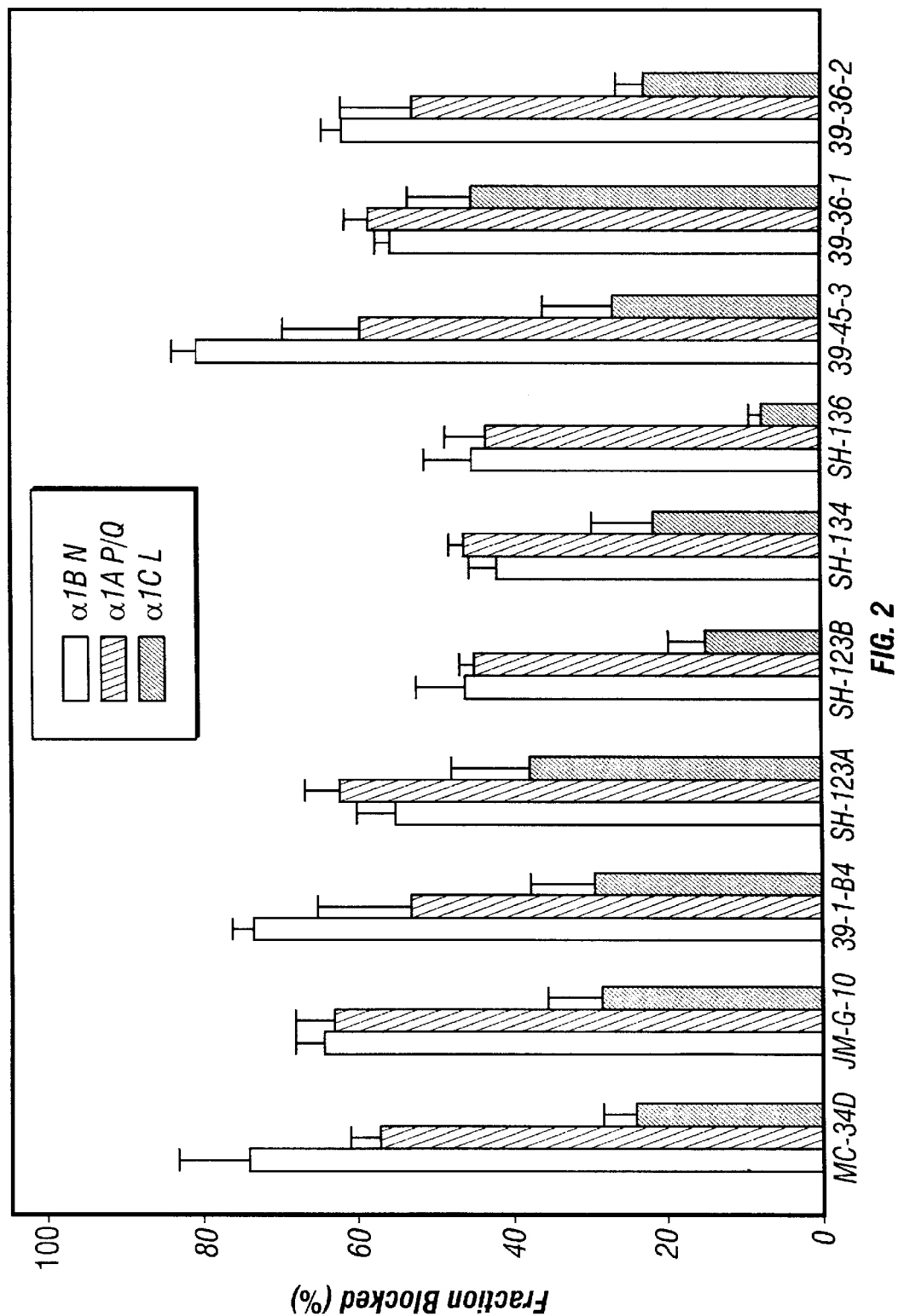
FIG. 2 is a graphic representation of the specificity of the compounds shown in FIG. 1 with respect to N-type, L-type and P/Q-type channels.
Figure 3:
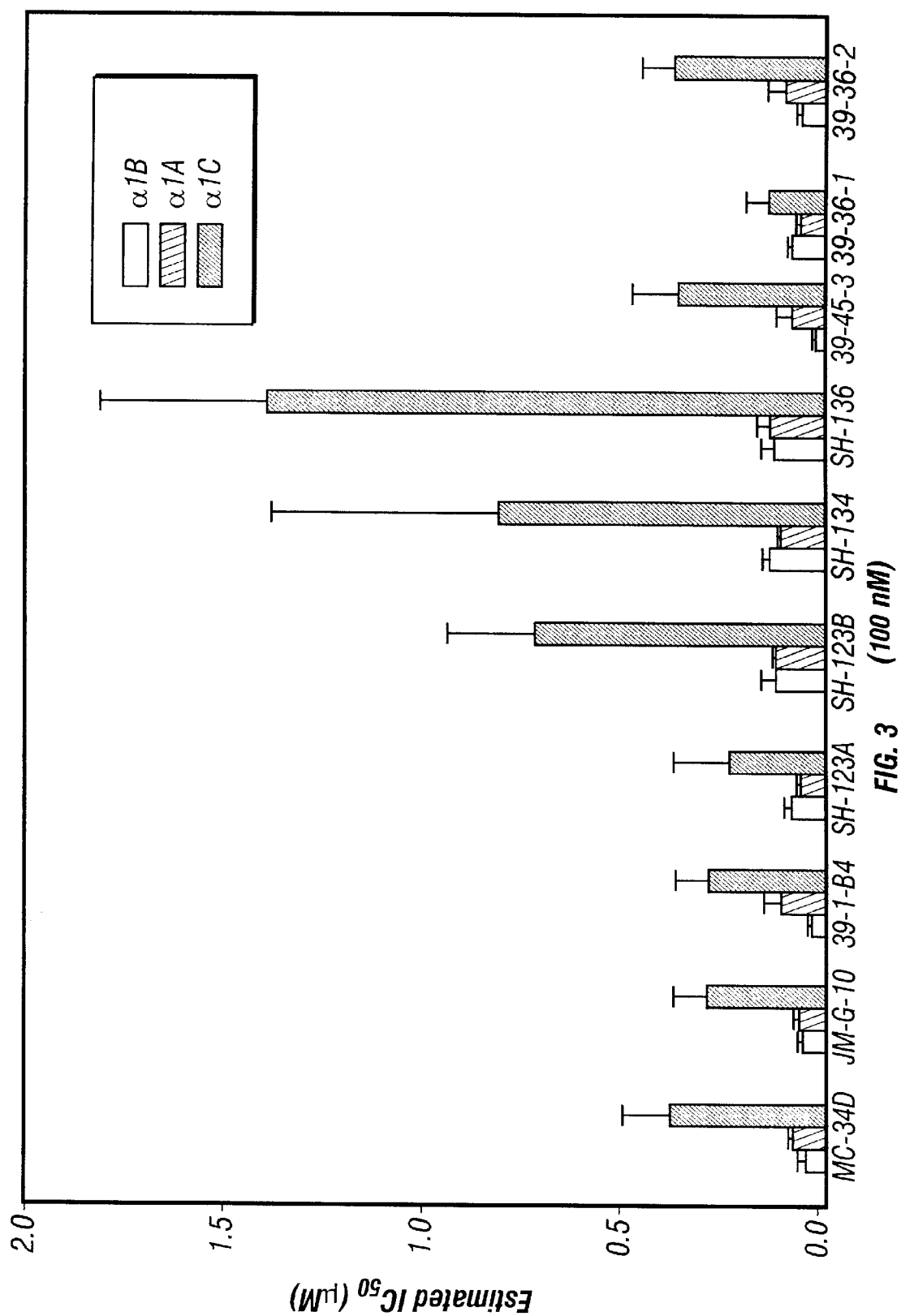
FIG. 3 is a graphic representation of the data shown in FIG. 2 based on IC$_{50}$ values calculated from the data shown in FIG. 2.

These results are shown graphically in FIGS. 2 and 3.

What is claimed is:

1. A method to identify a blocker of ion channel activity which method comprises contacting cells which display an ion channel of interest with a candidate compound under conditions wherein activation of said ion channel would occur in the absence of said compound; and assessing the ability of said candidate compound to inhibit said activation whereby a candidate compound whose presence results in inhibition of activation is identified as a blocker of said ion channel, and wherein said library comprises compounds of the formula

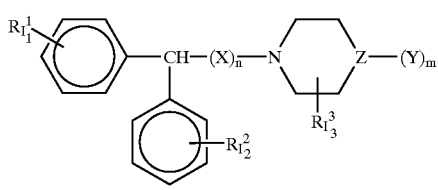

(1)

wherein m is 0, 1 or 2;

wherein when m is 0, Z is 0, when m is 1, Z is N, and when m is 2, Z is C;

Y is H, OH, $NH_2$, or an organic moiety of 1–20C, optionally additionally containing 1–8 heteroatoms selected from the group consisting of N, P, O, S and halo;

each $l^1$ and $l^2$ is independently 0–5;

$l^3$ is 0 or 1;

each of $R^1$, $R^2$ and $R^3$ is independently alkyl (1–6C), aryl (6–10C) or arylalkyl (7–16C) optionally containing 1–4 heteroatoms selected from the group consisting of halo, N, P, O, and S or each of $R^1$ and $R^2$ may independently be halo, COOR, $CONR_2$, $CF_3$, CN or $NO_2$, wherein R is H or lower alkyl (1–4C) or alkyl (1–6C);

n is 0 or 1; and

X is a linker.

2. A method to identify a compound which is a blocker of ion channel activity which method comprises contacting a cell which displays said ion channel on its surface with a labeled compound known to bind said ion channel, said contacting in the presence and absence of said candidate compound and assessing the ability of said candidate compound to inhibit the binding of said labeled ligand, whereby a candidate compound whose presence results in inhibition of the binding of said ligand is identified as a blocker of said ion channel, and wherein said candidate compound is a member of a library which comprises compounds of the formula

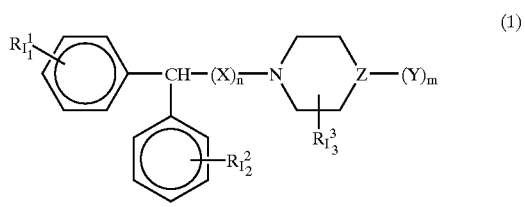

(1)

wherein m is 0, 1 or 2;

wherein when m is 0, Z is 0, when m is 1, Z is N, and when m is 2, Z is C;

Y is H, OH, $NH_2$, or an organic moiety of 1–20C, optionally additionally containing 1–8 heteroatoms selected from the group consisting of N, P, O, S and halo;

each $l^1$ and $l^2$ is independently 0–5;

$l^3$ is 0 or 1;

each of $R^1$, $R^2$ and $R^3$ is independently alkyl (1–6C), aryl (6–10C) or arylalkyl (7–16C) optionally containing 1–4 heteroatoms selected from the group consisting of halo, N, P, O, and S or each of $R^1$ and $R^2$ may independently be halo, COOR, $CONR_2$, $CF_3$, CN or $NO_2$, wherein R is H or lower alkyl (1–4C) or alkyl (1–6C);

n is 0 or 1; and

X is a linker.

* * * * *